US009867997B2

(12) United States Patent
Boutoussov et al.

(10) Patent No.: US 9,867,997 B2
(45) Date of Patent: Jan. 16, 2018

(54) HANDPIECE ASSEMBLY FOR LASER TREATMENT DEVICE

(71) Applicant: BIOLASE, Inc., Irvine, CA (US)

(72) Inventors: Dmitri Boutoussov, Dana Point, CA (US); Rolf G. Kojima, San Clemente, CA (US)

(73) Assignee: BIOLASE, INC., Irvine, CA (US)

( * ) Notice: Subject to any disclaimer, the term of this patent is extended or adjusted under 35 U.S.C. 154(b) by 453 days.

(21) Appl. No.: 14/060,877

(22) Filed: Oct. 23, 2013

(65) Prior Publication Data

US 2014/0113243 A1    Apr. 24, 2014

Related U.S. Application Data

(60) Provisional application No. 61/717,956, filed on Oct. 24, 2012, provisional application No. 61/777,112, filed on Mar. 12, 2013.

(51) Int. Cl.
*A61C 1/00* (2006.01)
*A61B 18/20* (2006.01)
(Continued)

(52) U.S. Cl.
CPC ............ *A61N 5/0613* (2013.01); *A61B 18/20* (2013.01); *A61C 1/0015* (2013.01);
(Continued)

(58) Field of Classification Search
CPC ......... A61C 1/088; A61C 1/01; A61C 19/004; A61C 19/06; A61C 19/063; A61B 18/20;
(Continued)

(56) References Cited

U.S. PATENT DOCUMENTS 4,826,431 A * 5/1989 Fujimura ............... A61B 18/22
433/215
4,940,411 A * 7/1990 Vassiliadis ............. A61B 18/20
433/215
(Continued)

FOREIGN PATENT DOCUMENTS

EP    780097    6/1997
EP    2911604    9/2015
(Continued)

OTHER PUBLICATIONS

International Search Report and Written Opinion issued Jan. 16, 2014 in related/corresponding PCT Patent Application No. PCT/US2013/66355 filed Oct. 23, 2013.
(Continued)

*Primary Examiner* — Ahmed Farah
(74) *Attorney, Agent, or Firm* — Greenberg Traurig LLP

(57) ABSTRACT

A handpiece assembly for laser treating a target surface and a laser system are disclosed. A handpiece assembly for laser treating a target surface includes a cable connector that is detachably coupled to a power supply and control module. The cable connector is configured to receive power and control signals from the power supply and control module. The handpiece assembly includes a laser module configured to receive the power and control signals from the cable connector and to generate electromagnetic energy based on the received power and control signals. The laser module is a replaceable module that is detachably coupled to the cable connector and a handpiece. The replaceable module allows a particular laser module to be removed from the handpiece assembly and replaced with another laser module. The handpiece assembly further includes the handpiece configured to receive the electromagnetic energy from the laser
(Continued)

module and to direct the electromagnetic energy to the target surface.

9 Claims, 6 Drawing Sheets

(51) Int. Cl.
| | |
|---|---|
| *A61N 5/06* | (2006.01) |
| *B23K 26/00* | (2014.01) |
| *A61C 13/15* | (2006.01) |
| *A61C 19/06* | (2006.01) |
| *A61C 19/08* | (2006.01) |
| *A61C 1/08* | (2006.01) |
| *A61B 18/22* | (2006.01) |
| *A61B 18/00* | (2006.01) |
| *A61N 5/067* | (2006.01) |
| *B23K 103/00* | (2006.01) |
| *A61B 17/00* | (2006.01) |
| *A61B 90/98* | (2016.01) |
| *A61B 90/00* | (2016.01) |

(52) U.S. Cl.
CPC .......... *A61C 1/0023* (2013.01); *A61C 1/0038* (2013.01); *A61C 1/0046* (2013.01); *A61C 1/0061* (2013.01); *A61C 1/081* (2013.01); *A61C 19/004* (2013.01); *A61C 19/06* (2013.01); *A61C 19/066* (2013.01); *A61C 19/08* (2013.01); *B23K 26/0006* (2013.01); *B23K 26/0096* (2013.01); *A61B 90/98* (2016.02); *A61B 2017/00973* (2013.01); *A61B 2018/0091* (2013.01); *A61B 2018/00702* (2013.01); *A61B 2018/00708* (2013.01); *A61B 2018/00779* (2013.01); *A61B 2018/00815* (2013.01); *A61B 2018/00988* (2013.01); *A61B 2018/202* (2013.01); *A61B 2018/2025* (2013.01); *A61B 2018/2065* (2013.01); *A61B 2018/225* (2013.01); *A61B 2090/0813* (2016.02); *A61C 2204/005* (2013.01); *A61N 5/062* (2013.01); *A61N 2005/0606* (2013.01); *A61N 2005/067* (2013.01); *A61N 2005/0644* (2013.01); *A61N 2005/0651* (2013.01); *A61N 2005/0659* (2013.01); *A61N 2005/0663* (2013.01); *B23K 2203/32* (2015.10)

(58) Field of Classification Search
CPC ............ A61B 18/22; A61B 2018/2015; A61B 2018/202; A61B 1/06; A61B 1/24
USPC .......... 433/29–31, 50, 51, 98, 99, 141–147; 606/10–14
See application file for complete search history.

(56) References Cited

U.S. PATENT DOCUMENTS

| | | | |
|---|---|---|---|
| 4,979,180 A | 12/1990 | Muncheryan | |
| 5,074,861 A * | 12/1991 | Schneider | A61F 9/008 600/2 |
| 5,228,852 A * | 7/1993 | Goldsmith | A61C 1/0046 433/141 |
| 5,662,644 A | 9/1997 | Swor | |
| 5,846,080 A * | 12/1998 | Schneider | A61C 1/0046 433/215 |
| 6,350,123 B1 * | 2/2002 | Rizoiu | B23K 26/146 433/29 |
| 7,632,264 B2 * | 12/2009 | Schafer | A61B 18/20 433/29 |
| 8,236,036 B1 | 8/2012 | Frost | |
| 9,072,572 B2 * | 7/2015 | Gill | A61C 19/004 |
| 2007/0150030 A1 | 6/2007 | Pearl et al. | |
| 2008/0077198 A1 | 3/2008 | Webb et al. | |
| 2010/0167226 A1 | 7/2010 | Altshuler et al. | |
| 2011/0144410 A1 | 6/2011 | Kennedy | |
| 2014/0272771 A1 * | 9/2014 | Boutoussov | A61C 1/0046 433/29 |

FOREIGN PATENT DOCUMENTS

| | | |
|---|---|---|
| ES | 2549832 | 11/2015 |
| JP | 2015-533579 | 11/2015 |
| WO | 1997043008 | 11/1997 |
| WO | 2014066489 | 5/2014 |

OTHER PUBLICATIONS

Australian Government, IP Australia; Examination Report No. 1 for Standard Patent Application, Issued in connection to AU2013334662; Jan. 20, 2017; 4 pages; Australia.
European Patent Office; European Search Report, Issued in Connection to EP13849355.6; dated May 24, 2016; 13 pages; Europe.
European Patent Office; Communication Pursuant to Article 94(3) EPC with Annex, Issued in Connection to EP13849355.6; dated Mar. 27, 2017; 6 pages; Europe.
Spanish Patent Office; Search Report, Issued in Connection to ES201590035; dated Mar. 1, 2017; 4 pages; Spain.
Japanese Patent Office; Translation of: Notificaiton of Reason for Rejection, Issued in Connection to JP2015-539752; Apr. 24, 2017; 2 pages; Japan.

* cited by examiner

HANDPIECE ASSEMBLY FOR LASER TREATMENT DEVICE

CROSS-REFERENCE TO RELATED APPLICATIONS

This application claims priority to U.S. Provisional Patent Application No. 61/717,956, filed Oct. 24, 2012, entitled "Laser Module for a Dental Chair Terminal," and to U.S. Provisional Patent Application No. 61/777,112, filed Mar. 12, 2013, entitled "Interchangeable Laser Module for a Dental Chair Terminal," which are herein incorporated by reference in their entireties.

TECHNICAL FIELD

The technology described herein relates generally to a laser treatment device and more particularly to a replaceable handpiece assembly for delivering electromagnetic energy to a target surface.

BACKGROUND

Electromagnetic energy devices are employed in a variety of applications. For example, a simple incandescent light may be used to illuminate an area with electromagnetic energy in a form of visible light. Another form of electromagnetic energy, such as a laser beam, may be used to illuminate an area, to identify a target, or to deliver concentrated energy to a target in order to perform various procedures such as melting, cutting, or the like. Certain medical devices may deliver electromagnetic energy to a target surface such as, for example, an eye, in order to correct a deficiency in visual acuity. Other medical devices may direct electromagnetic energy toward a surface of a tooth to perform, for example, a cutting or whitening operation. Endoscopic devices can be used to enhance visualization of internal parts of, for example, a human body in order to detect or remove diseased tissue.

SUMMARY

A handpiece assembly for laser treating a target surface and a laser system are disclosed. A handpiece assembly for laser treating a target surface includes a cable connector that is detachably coupled to a power supply and control module. The cable connector is configured to receive power and control signals from the power supply and control module. The handpiece assembly also includes a laser module configured to receive the power and control signals from the cable connector and to generate electromagnetic energy based on the received power and control signals. The laser module is a replaceable module that is detachably coupled to the cable connector and a handpiece to allow the laser module to be removed from the handpiece assembly. The replaceable module allows a particular laser module to be removed from the handpiece assembly and replaced with another laser module. The handpiece assembly further includes the handpiece configured to receive the electromagnetic energy from the laser module and to direct the electromagnetic energy to the target surface through a replaceable tip attachment.

In another example, a laser system includes a power supply and control module configured to provide power and control signals to a handpiece assembly. The power supply and control module is detachably coupled to the handpiece assembly via a cable. The laser system further includes a handpiece assembly, where the handpiece assembly includes a cable connector that is detachably coupled to the power supply and control module via the cable. The cable connector is configured to receive the power and control signals from the power supply and control module. The handpiece assembly also includes a laser module configured to receive the power and control signals from the cable connector and to generate electromagnetic energy based on the received power and control signals. The handpiece assembly further includes a handpiece configured to receive the electromagnetic energy from the laser module and to direct the electromagnetic energy to a target surface.

DETAILED DESCRIPTION

Figure 1:
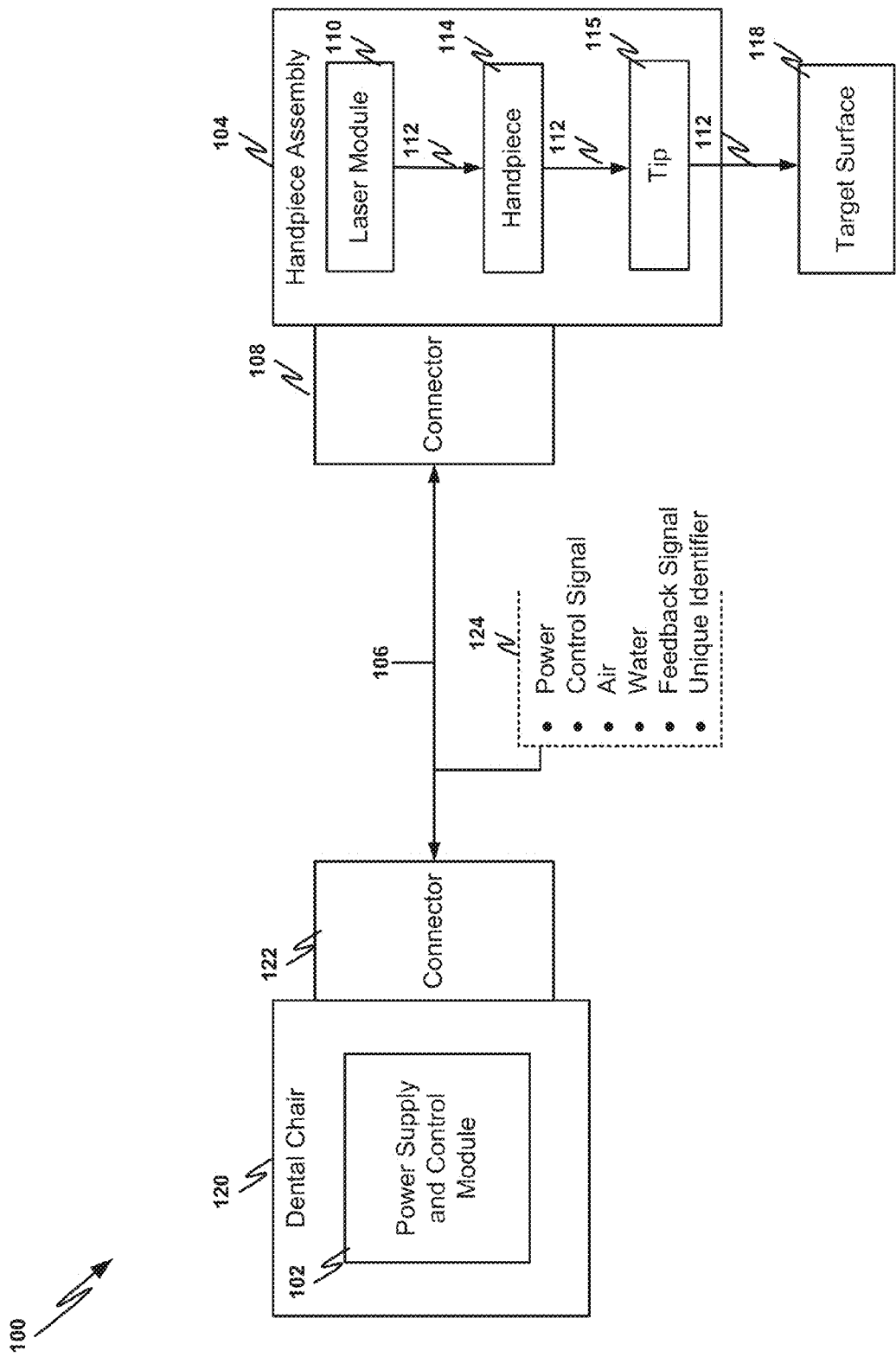
FIG. 1 depicts an example laser system including a power supply and control module included in a dental chair and a handpiece assembly connected to the power supply and control module.

FIG. 1 depicts an example laser system 100 including a power supply and control module 102 included in a dental chair 120 and a handpiece assembly 104 connected to the power supply and control module 102. In the example laser system 100, the power supply and control module 102 is used to provide power and control signals to the handpiece assembly 104 via a cable 106. For example, the power provided by the power supply and control system 102 may include a DC voltage that is used to provide a driving current to a laser module 110 included in the handpiece assembly 104. The control signals provided by the power supply and control module 102 to the handpiece assembly 104 include various electronic signals for controlling operation of the laser module 110. For example, the control signals may be used to turn the laser module 110 on, shut the laser module 110 off, control a maximum output power that can be provided by the laser module 110, or to control various other aspects of the handpiece assembly 104. The power supply and control module 102 is mounted inside or on an instrument terminal of the dental chair 120.

The handpiece assembly 104 includes a cable connector 108, the laser module 110, a handpiece 114, and a tip 115. The cable connector 108 is detachably coupled to the power supply and control module 102 via the cable 106 and is used to receive the power and control signals from the power supply and control module 102. The cable connector 108 thus includes the necessary connections to receive the power and control signals and to thereafter distribute the received power and control signals to other portions of the handpiece assembly 104. It is noted that although the example illustration of FIG. 1 depicts the cable connector 108 as being separate from the handpiece assembly 104, in other examples, the cable connector 108 is integrated within the handpiece assembly 104 and is considered a part of the handpiece assembly in such other examples.

The laser module 110 of the handpiece assembly 104 is connected to the cable connector 108 and is configured to receive the power and control signals from the cable connector 108. Based on the received power and control signals, the laser module 110 generates electromagnetic energy 112 (e.g., laser light). The laser module 110 may be, for example, a laser diode, a diode-pumped solid state laser, a flashlamp-pumped solid state laser, a light emitting diode, or another type of light-generating component. The handpiece 114 receives the electromagnetic energy 112 from the laser module 110 and directs the electromagnetic energy 112 to a target surface 118. In the example of FIG. 1, the target surface may be an area of a dental patient's mouth (e.g., teeth, gums, etc.). The handpiece 114 is application-specific and may thus include a geometry or optics (e.g., lenses, etc.) that are specific for a particular clinical application. In directing the electromagnetic energy 112 to the target surface 118, the tip 115 is used. The tip 115 receives the electromagnetic energy 112 from the handpiece 114 and may include fiber optic materials, sapphire, or other optical materials. Further, the tip 115 may be shaped to be optimized for a particular clinical application.

As described above, the handpiece assembly 104 includes the cable connector 108 that is detachably coupled to the power supply and control module 102 and is used to receive the power and control signals from the power supply and control module 102. The cable connector 108 is designed to match a cable connector 122 included on the dental chair 120, such that various signals and substances are transported between the dental chair 120 and handpiece assembly 104 over the cable 106. As illustrated at 124, the signals and substances transported over the cable 106 include the aforementioned power and control signals and also include pressurized air, water or another liquid, a feedback signal, and a unique identifier.

The cable 106 includes the connections necessary to allow communication in both directions between the dental chair 120 and the handpiece assembly 104. Thus, communications from the dental chair 120 to the handpiece assembly 104 include the power and control signals that are received at the cable connector 108 and used by the laser module 110 in generating the electromagnetic energy 112. The cable 106 also includes an air channel or a water channel for delivering the pressurized air or water from the dental chair 120 to the handpiece assembly 104. The pressurized air or water is used at the handpiece assembly 104 to cool the laser module 110 or to provide an air or water spray at or around the target surface 118.

Communications from the handpiece assembly 104 to the dental chair 120 include the aforementioned feedback signal. The feedback signal includes various operation conditions of the laser module 110, which may indicate, for example, an output power of the laser module 110, a temperature of the laser module 110, or a presence of other signals for diagnostic applications. In one example, the handpiece assembly 104 includes a microprocessor with instructions for controlling output parameters of the laser module 110 (e.g., controlling an output power of the laser module 110) and for monitoring operation conditions of the laser module 110. The instructions of the microprocessor are received from the power supply and control module 102 via the cable 106. In examples where the microprocessor is included in the handpiece assembly 104, the feedback signal includes various operation conditions of the laser module 110 that are monitored by the microprocessor.

Communications from the handpiece assembly 104 to the dental chair 120 also include the aforementioned unique identifier. In an example, the laser module 110 includes a unique electronic identifier. The electronic identifier includes information about the type of laser included in the laser module 110 and calibration parameters of the laser module 110. By transmitting the unique identifier for the laser module 110 to the power supply and control module 102, safeguards are triggered within the power supply and control module 102 to protect the laser module 110. For example, the unique identifier is used to indicate a maximum driving current that may be received by the laser module 110, such that the power supply and control module 102 can constrain the driving current supplied based on this value. Further, the unique identifier is used generally for identification of the laser module 110 by the dental chair 120 or the power supply and control module 102.

Conventionally, laser systems for dental or medical applications include laser modules positioned in one of two typical configurations. In a first typical configuration, the laser module is positioned in a system housing. In this configuration, both the power supply and control module and the laser module are included in the system housing, and a delivery system is used for delivering electromagnetic energy from the system housing to a delivery device. For example, in the first typical configuration, the electromagnetic energy is generated in the housing, and a fiber cable is used to deliver the generated electromagnetic energy to a handpiece assembly. In a second typical configuration, the laser module is included in a handpiece assembly, where the handpiece assembly also includes a power supply and control module. Thus, in the second typical configuration, all portions of the laser system (e.g., a battery to be used as a power supply, necessary controls, and the laser module used to generate the electromagnetic energy based on the current supplied by the battery) are integrated within the single handpiece assembly.

By contrast, the laser system 100 utilizes a hybrid configuration that differs from both of the typical configurations described above. In the hybrid configuration, the power supply and control module 102 is physically separated from the laser module 110. As described above, the handpiece assembly 104 including the laser module 110 is separate and distinct from the power supply and control module 102, such that the power supply and control module 102 is not integrated within the handpiece assembly 104. Thus, in the laser system 100, the power supply and control module 102 is separated from both of the handpiece assembly 104 and laser module 110. Further, in the example laser system 100 of FIG. 1, the cable 106 does not include a fiber cable, such that the laser system 100 differs from embodiments of the first typical configuration that use a fiber cable as a delivery system. In an example of the laser system 100, no fiber cables are used in any portion of the system 100.

In the hybrid configuration of the laser system 100, the handpiece assembly 104 (including the cable connector 108, the laser module 110, and the handpiece 114) is a replaceable, interchangeable module. The replaceable, interchangeable nature of the handpiece assembly 104 allows a particular handpiece assembly to be disconnected from the system 100 and replaced with another handpiece assembly without requiring replacement of the power supply and control module 102. The replaceable, interchangeable nature of the handpiece assembly 104 is facilitated by the cable connector 108 of the handpiece assembly 104, which allows the handpiece assembly 104 to be detachably coupled to the power supply and control module 102. The detachable coupling allows the handpiece assembly 104 to be disconnected easily from the power supply and control module 102. Specifically, in an example, the handpiece assembly 104 is disconnected from the power supply and control module 102 by disconnecting the cable 106 from the power supply and control module 102.

To further facilitate the replaceable, interchangeable nature of the handpiece assembly 104, the laser system 100 of FIG. 1 utilizes standardized connectors for the connectors 108, 122. In this manner, any handpiece assembly 104 including the proper standardized connector can be swapped into and out of the laser system 100, thus allowing handpiece assemblies with different parameters (e.g., handpiece assemblys configured to generate electromagnetic energy 112 of different wavelengths) to be easily connected and disconnected from the system 100. The standardized connectors between the handpiece assembly 104 and the dental chair 120 also prevent operation of unknown or unauthorized devices within the system 100. For example, the standardized connectors may have a unique design to ensure that unauthorized or noncompliant instruments or laser modules cannot be connected to the system 100.

Figure 2A:
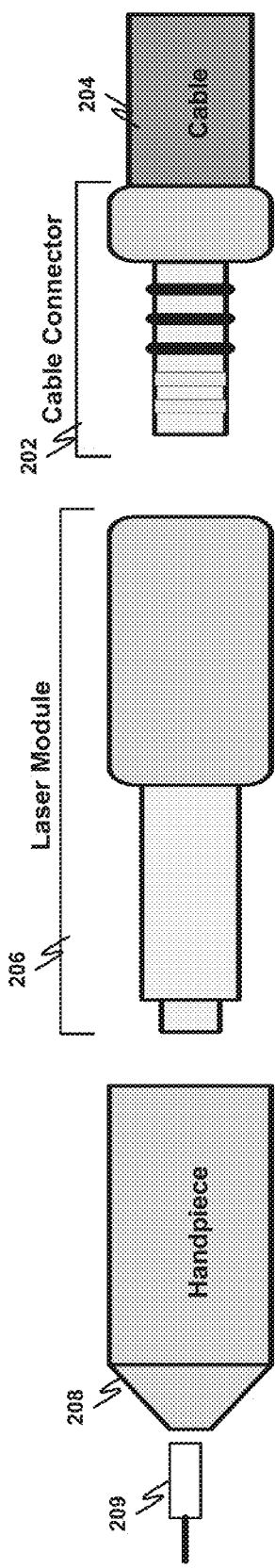
FIG. 2A depicts an example handpiece assembly including a cable connector, a laser module, a handpiece, and a tip.
Figure 2B:
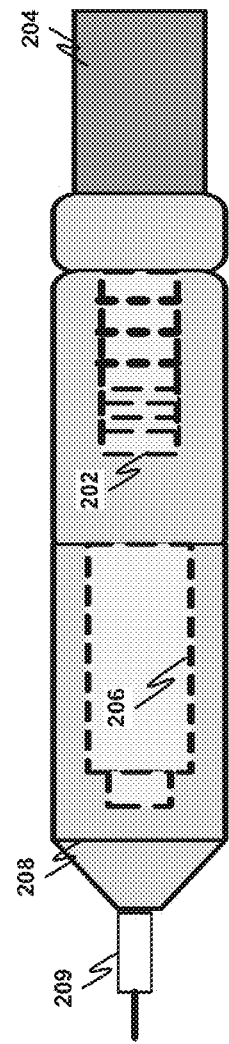
FIG. 2B depicts an example handpiece assembly including a cable connector, a laser module, a handpiece, and a tip, showing the constituent pieces connected to each other to form a single unit.

FIGS. 2A and 2B depict an example handpiece assembly including a cable connector 202, a laser module 206, a handpiece 208, and a tip 209. In FIG. 2A, the constituent pieces 202, 206, 208, 209 of the handpiece assembly are disassembled, and in FIG. 2B, the constituent pieces 202, 206, 208, 209 are connected to each other to form a single handpiece assembly unit. The cable connector 202 is detachably connected to a power supply and control module via a cable 204 (e.g., as illustrated in the example laser system 100 of FIG. 1). The cable connector 202 is used to receive power and control signals from the power supply and control module. The laser module 206 is connected to the cable connector 202 and is used to receive the power and control signals from the cable connector 202. Based on the power and control signals, the laser module 206 generates electromagnetic energy. The handpiece 208 is connected to the laser module 206 and receives the electromagnetic energy from the laser module 206. The handpiece 208 is used to direct the electromagnetic energy to a target surface (e.g., a tissue surface or other part of a human body). In directing the electromagnetic energy to the target surface, the electromagnetic energy is passed through the tip 209, which may have a geometry that is optimized for a particular clinical application.

In FIGS. 2A and 2B, the cable 204 includes air and water channels and electrical connections for delivering pressurized air, water, and the power and control signals. The laser module 206 may include a laser diode, a diode-pumped solid state laser, a flashlamp-pumped solid state laser, or a light emitting diode. The laser module 206 generates electromagnetic energy at a wavelength in the range of approximately 400 nm to 3.0 μm and with an average power in a range of approximately 0.1 W to 20 W. The laser module 206 operates in a continuous-wave (CW) mode or a pulsed operation mode.

In one example, the handpiece 208 is a rotatable handpiece that is designed for a specific application. The handpiece 208 may include optical elements (e.g., a lens, mirror, filter, beamsplitter, prism, grating, etc.) or the handpiece may have no permanent optics. The handpiece 208 may be autoclavable, or the handpiece 208 may be disinfected with a disinfecting solution or used with a sterile sleeve or cover.

Figure 3:
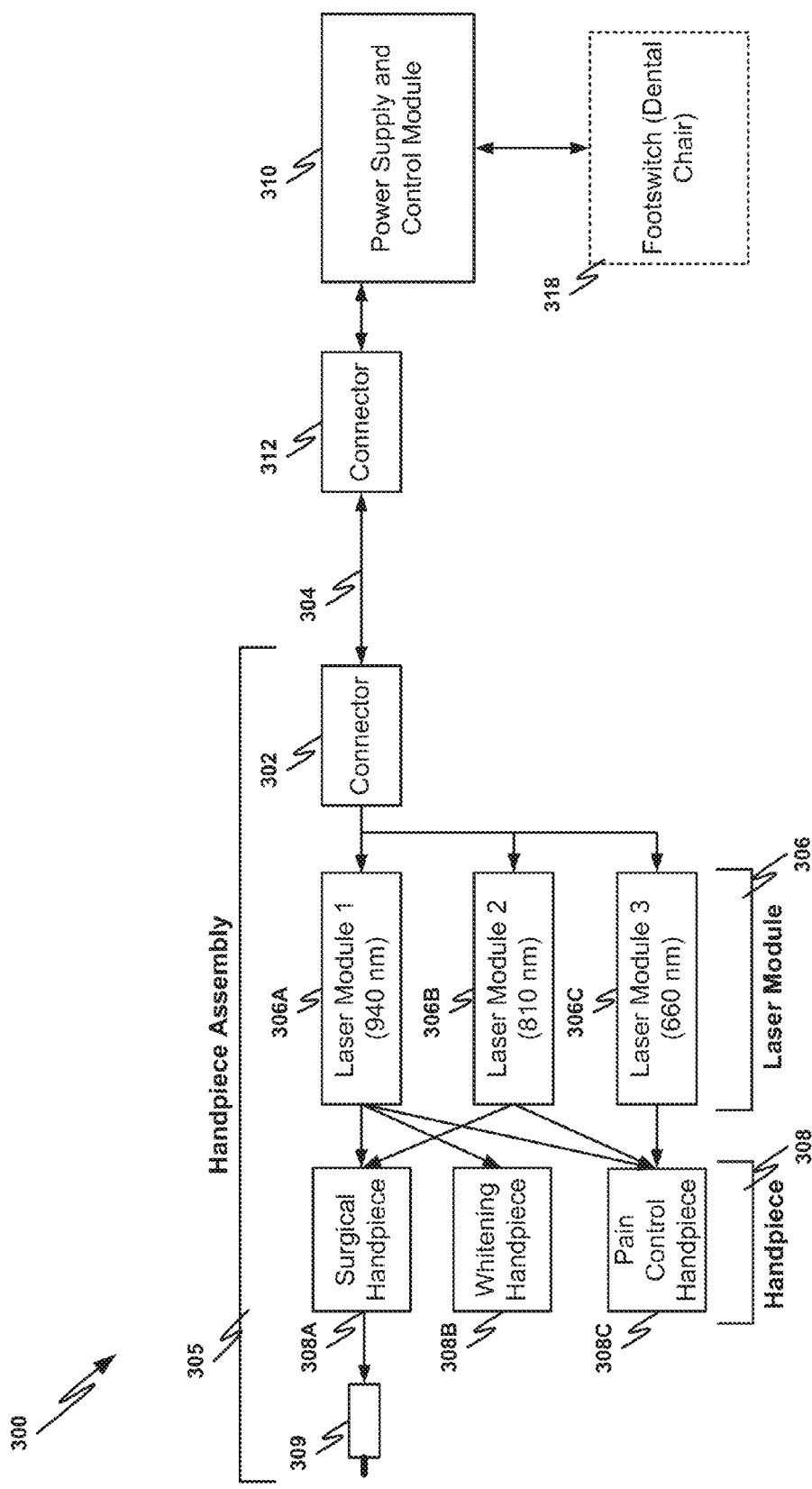
FIG. 3 depicts an example laser system including a variety of interchangeable laser modules and a variety of interchangeable handpieces.

FIG. 3 depicts an example laser system 300 including a variety of interchangeable laser modules 306A, 306B, 306C and a variety of interchangeable handpieces 308A, 308B, 308C. In the example laser system 300, a power supply and control module 310 is used to provide power and control signals to a handpiece assembly 305 via a cable 304. The handpiece assembly 305 includes a cable connector 302, a laser module 306, a handpiece 308, and a tip 309. The cable connector 302 is detachably coupled to the power supply and control module 310 via the cable 304 and is used to receive the power and control signals from the power supply and control module 310. The cable connector 302 matches a cable connector 312 of the power supply and control module 310. The laser module 306 of the handpiece assembly 305 receives the power and control signals from the cable connector 302 and generates electromagnetic energy, and the handpiece 308 receives the electromagnetic energy from the laser module 306. Because the power supply and control module 310 may be included within a dental chair, the laser system 300 further includes an optional footswitch 318. The footswitch 318 is used, for example, to actuate the laser output of the laser module 306.

The handpiece assembly 305 is a replaceable, interchangeable module. The replaceable, interchangeable nature of the handpiece assembly 305 allows a particular handpiece assembly to be disconnected from the system 300 and replaced with another handpiece assembly without requiring replacement of the power supply and control module 310. In a similar manner, both the laser module 306 and the handpiece 308 are also replaceable and interchangeable. The laser module 306 is detachably coupled to the cable connector 302 and to the handpiece 308. The detachable coupling between the laser module 306 and the cable connector 302 and the handpiece 308 allows the laser module 306 to be easily removed from the handpiece assembly 305. Further, due to the replaceable nature of the laser module 306, a particular laser module can be removed from the handpiece assembly 305 and replaced with another laser module without requiring replacement of any other components of the system 300 (e.g., without requiring replacement of the cable connector 302, the handpiece 308, or the power supply and control module 310).

The replaceable nature of the laser module 306 is highlighted in FIG. 3, which illustrates the variety of interchangeable laser modules 306A, 306B, 306C. The different laser modules 306A, 306B, 306C in the example of FIG. 3 each generate electromagnetic energy at a different wavelength. For example, the laser module 306A generates electromagnetic energy at a wavelength of 940 nm, the laser module 306B generates electromagnetic energy at a wavelength of 810 nm, and the laser module 306C generates electromagnetic energy at a wavelength of 660 nm. In a similar manner, the laser module 306 may be configured to work with different, interchangeable laser modules that utilize different laser types. For example, the interchangeable laser modules may include a laser module that utilizes a laser diode, a laser module that utilizes a diode-pumped solid state laser, a laser module that utilizes a flashlamp-pumped solid state laser, or a laser module that utilizes a light emitting diode.

As noted above, the handpiece 308 is also a replaceable and interchangeable module. The handpiece 308 is detachably coupled to the laser module 306. The detachable coupling between the handpiece 308 and the laser module 306 allows the handpiece 308 to be easily removed from the handpiece assembly 305. Further, due to the replaceable nature of the handpiece 308, a particular handpiece can be removed from the handpiece assembly 305 and replaced with another handpiece without requiring replacement of any other components of the system 300 (e.g., without requiring replacement of the cable connector 302, the laser module 306, or the power supply and control module 310).

The replaceable nature of the handpiece 308 is highlighted in FIG. 3, which illustrates the variety of interchangeable handpieces 308A, 308B, 308C. The different handpieces 308A, 308B, 308C in the example of FIG. 3 are each adapted for different clinical operations. For example, the handpiece 308A is adapted for performing surgery, the handpiece 308B is adapted for whitening teeth, and the handpiece 308C is adapted for a pain therapy clinical operation. The interchangeable handpieces 308A, 308B, 308C may also have different geometries, different optics, and other varying properties. As illustrated in FIG. 3, certain of the interchangeable laser modules 306A, 306B, 306C are usable with only certain of the interchangeable handpieces 308A, 308B, 308C, and vice versa. For example, although the laser module 306A is usable with each of the three handpieces 308A, 308B, 308C, the laser module 306C is usable with only the handpiece 308C. In other examples, however, all laser modules 306A, 306B, 306C are usable with all handpieces 308A, 308B, 308C, and vice versa. In the example of FIG. 3, the surgical handpiece 308A uses the replaceable tip 309. The whitening handpiece 308B and the pain control handpiece 308C do not use a tip but may use disposable protective covers.

The replaceable and interchangeable handpiece assembly 305, laser module 306, and handpiece 308 facilitate economical upgrading of the laser system 300. For example, a new laser module can replace a failing, old laser module, and this replacement does not require replacement of other components of the system 300.

Figure 4:
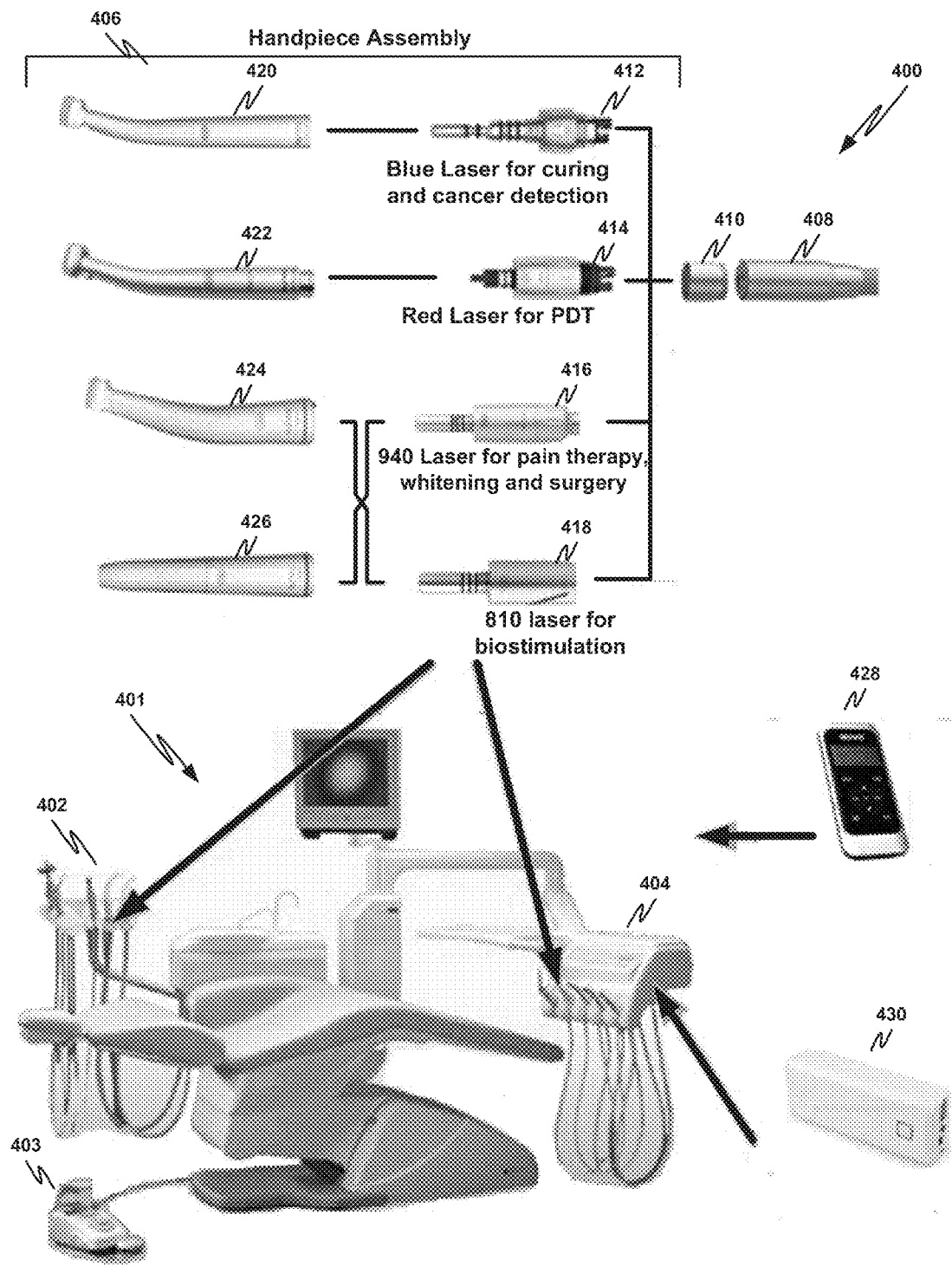
FIG. 4 depicts an example laser system for use with a dental chair.

FIG. 4 depicts an example laser system 400 for use with a dental chair 401. In the example laser system 400, a power supply and control module is integrated within a portion of the dental chair 401. A handpiece assembly 406 includes a cable connector 410, interchangeable laser modules 412, 414, 416, 418, and interchangeable handpieces 420, 422, 424, 426. The cable connector 410 is detachably coupled to the power supply and control module via the cable 408 and is used to receive power and control signals from the power supply and control module. The cable 408 includes an air channel or a water channel for delivering pressurized air or water from the dental chair 401 to the handpiece assembly 406. As illustrated in FIG. 4, the dental chair 401 includes a footswitch 403, which is used to actuate the laser output of the handpiece assembly 406.

The dental chair 401 further includes instrument terminals 402, 404. The instrument terminals 402, 404 are used to hold the handpiece assembly 406 when the handpiece assembly 406 is not in use. A sensor signal from one or both of the instrument terminals 402, 404 indicates whether the handpiece assembly 406 is within a holder included on the instrument terminal 402 or 404. The sensor signal is used in one example to automatically switch the laser system 400 between "standby" and "ready" modes, and a signal from the footswitch 403 may be used to actuate the laser output of the handpiece assembly 406 when the laser system 400 is in the "ready" mode. The dental chair 401 further includes a user interface that is configured to read a signal from the power supply and control module. The user interface is used to generate a display that indicates when the handpiece assembly 406 has been removed from the instrument terminals 402, 404.

The dental chair 401 includes wireless communication circuitry 430. For example, the power supply and control module includes the wireless communication circuitry 430, and the wireless communication circuitry 430 is used to receive a signal from a wireless remote control 428 or to communicate with a network. The wireless remote control 428 is used to actuate the laser output of the handpiece assembly 406, send various control signals from the power supply and control module to the handpiece assembly 406, or otherwise control one or more operations of the handpiece assembly 406. The wireless remote control 428 is, in an example, a smartphone or a tablet computer (e.g., running the Android operating system or the Apple iOS operating system) that is able to communicate in a wireless manner with the wireless communication circuitry 430. Although the wireless connection capabilities of the remote control 428 are described above, in other examples, the remote control 428 is a wired controller, such that the remote control 428 communicates with the dental chair 401 or the handpiece assembly 406 via a wired connection.

The handpiece assembly 406 is a replaceable, interchangeable module. Similarly, the laser module and the handpiece included within the handpiece assembly 406 are also replaceable and interchangeable, such that both the laser module and the handpiece can be easily removed from the handpiece assembly 406 and replaced with another compatible laser module and handpiece, respectively. The replaceable nature of the laser module is highlighted in FIG. 4, which illustrates the variety of interchangeable laser modules 412, 414, 416, 418. The different laser modules 412, 414, 416, 418 each generate electromagnetic energy at a different wavelength and are adapted for different clinical operations. For example, the laser module 412 generates blue laser light that is useful for cancer detection and curing of dental composite materials; the laser module 414 generates red laser light that is useful for photoradiation therapy or photodynamic therapy (PDT); the laser module 416 generates laser light at 940 nm that is useful for pain therapy, teeth whitening, and surgery applications; and the laser module 418 generates laser light at 810 nm that is useful for biostimulation applications.

The handpiece is also a replaceable and interchangeable module. The replaceable nature of the handpiece is highlighted in FIG. 4, which illustrates the variety of interchangeable handpieces 420, 422, 424, and 426. The different handpieces 420, 422, 424, 426 are application specific, such that they are adapted for different clinical operations. For example, the handpiece 420 is used with the laser module 412 for cancer detection and curing of dental composite materials; the handpiece 422 is used with the laser module 414 for performing photoradiation therapy or photodynamic therapy (PDT); the handpiece 424 is used with the laser module 416 or the laser module 418 and is adapted for performing clinical operations at the wavelength ranges of the modules 416, 418; and the handpiece 426 is used with the laser module 416 or the laser module 418 and is adapted for performing clinical operations at the wavelength ranges of the modules 416, 418.

Figure 5:
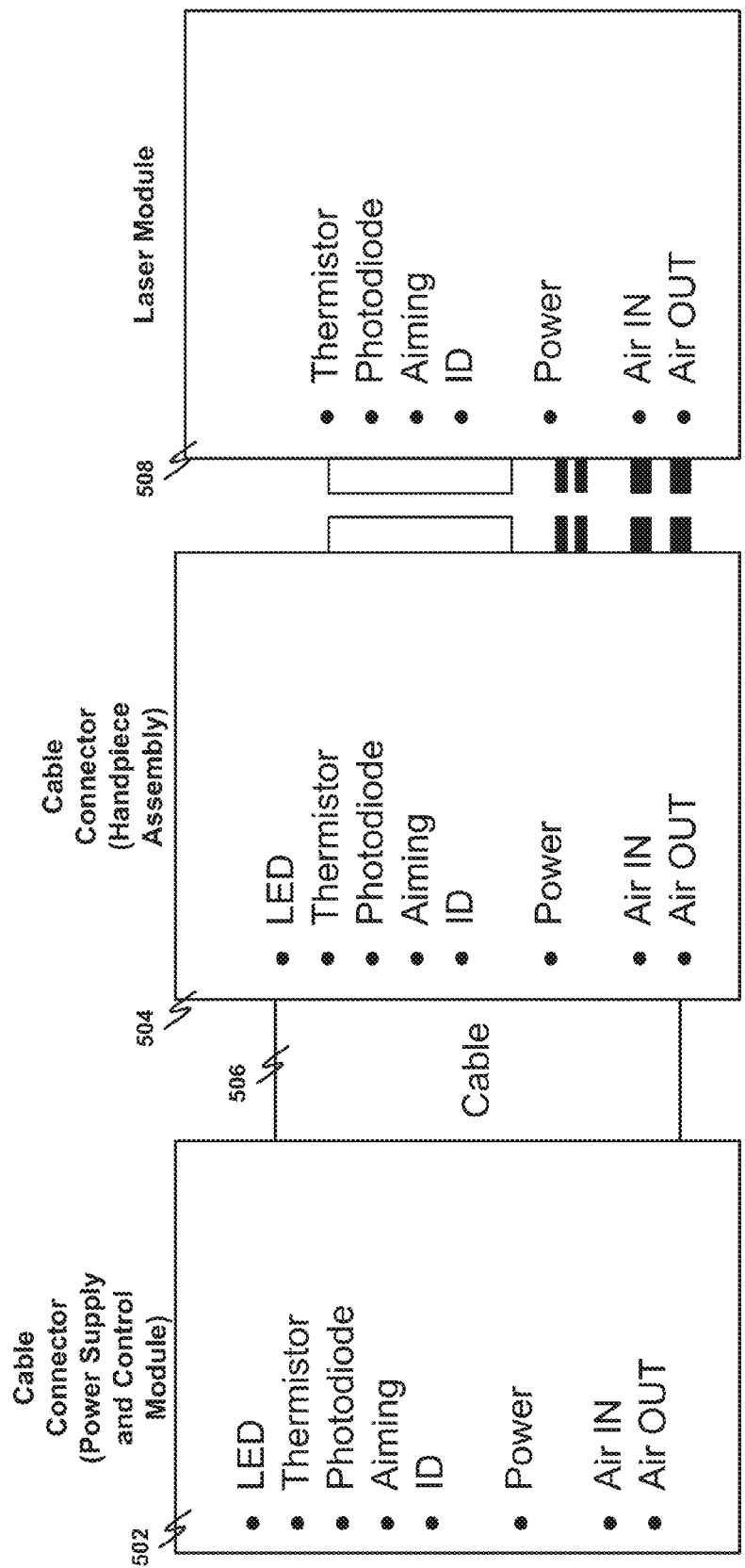
FIG. 5 depicts example cable connectors that are used in connecting a power supply and control module, a handpiece assembly, and a laser module included in the handpiece assembly.

FIG. 5 depicts example cable connectors 502, 504, 508 that are used in connecting a power supply and control module, a handpiece assembly, and a laser module included in the handpiece assembly. The handpiece assembly includes the cable connector 504, and the cable connector 504 is detachably coupled to the cable connector 502 of the power supply and control module via a cable 506. The cable connector 504 is used to receive power and control signals from the power supply and control module. The cable connector 504 thus includes the necessary connections to receive the power and control signals and to thereafter distribute the received power and control signals to other portions of the handpiece assembly.

The cable connector 504 of the handpiece assembly is designed to match the cable connector 502 of the power supply and control module. With the matching connectors 502, 504, various signals and substances are transported between the power supply and control module (or a dental chair that houses the power supply and control module) and the handpiece assembly. The connectors 502, 504 are standardized connectors, and any handpiece assembly including the proper standardized connector can be swapped into and out of the system. This allows handpiece assemblies with different parameters to be easily connected and disconnected from the system. The standardized connectors 502, 504 also prevent operation of unknown or unauthorized devices within the system.

As illustrated in FIG. 5, the standardized connectors 502, 504 include connections or channels for transferring a laser power control signal ("Power"), air intake and output ("Air IN" and "Air OUT"), an identification code signal ("ID"), a signal from a thermistor ("Thermistor"), a signal from a photodiode ("Photodiode"), a signal from a light emitting diode ("LED"), and an aiming beam ("Aiming"). The signal from the thermistor is provided from a thermistor included within or near the laser module. The signal from the thermistor is an example of a feedback signal that is transmitted from the handpiece assembly to the power supply and control module. The signal from the photodiode is provided from a photodiode included within or near the laser module. The signal from the photodiode is another feedback signal used to indicate an output power of the laser module. Similarly, the identification code signal is a feedback signal sent from the laser module to the power supply and control module and is used to identify the laser module included in the handpiece assembly. In contrast to the aforementioned feedback signals, the aiming beam is transmitted from the power supply and control module to the handpiece assembly. The aiming beam is a visible light beam that may be used in aiming the output of the laser module. The signal from the light emitting diode is also transmitted from the power supply and control module to the handpiece assembly and may be used to indicate that the system is in a "ready" mode (e.g., the signal may turn on LEDs at the handpiece assembly and the power supply and control module to indicate the "ready" mode).

The cable 506 includes integrated electrical and air lines to ensure flexibility of a user's movements (e.g., to ensure flexibility of a dentist's movements within an operating area). The cable connector 504 of the handpiece assembly also matches the connector 508 of the laser module, such that the aforementioned signals and substances (e.g., the signal from the thermistor, the signal from the photodiode, the aiming beam, the identification code signal, the laser power control signal, and the air intake and output) can be transferred between the laser module and the cable connector 504 of the handpiece assembly.

Figure 6:
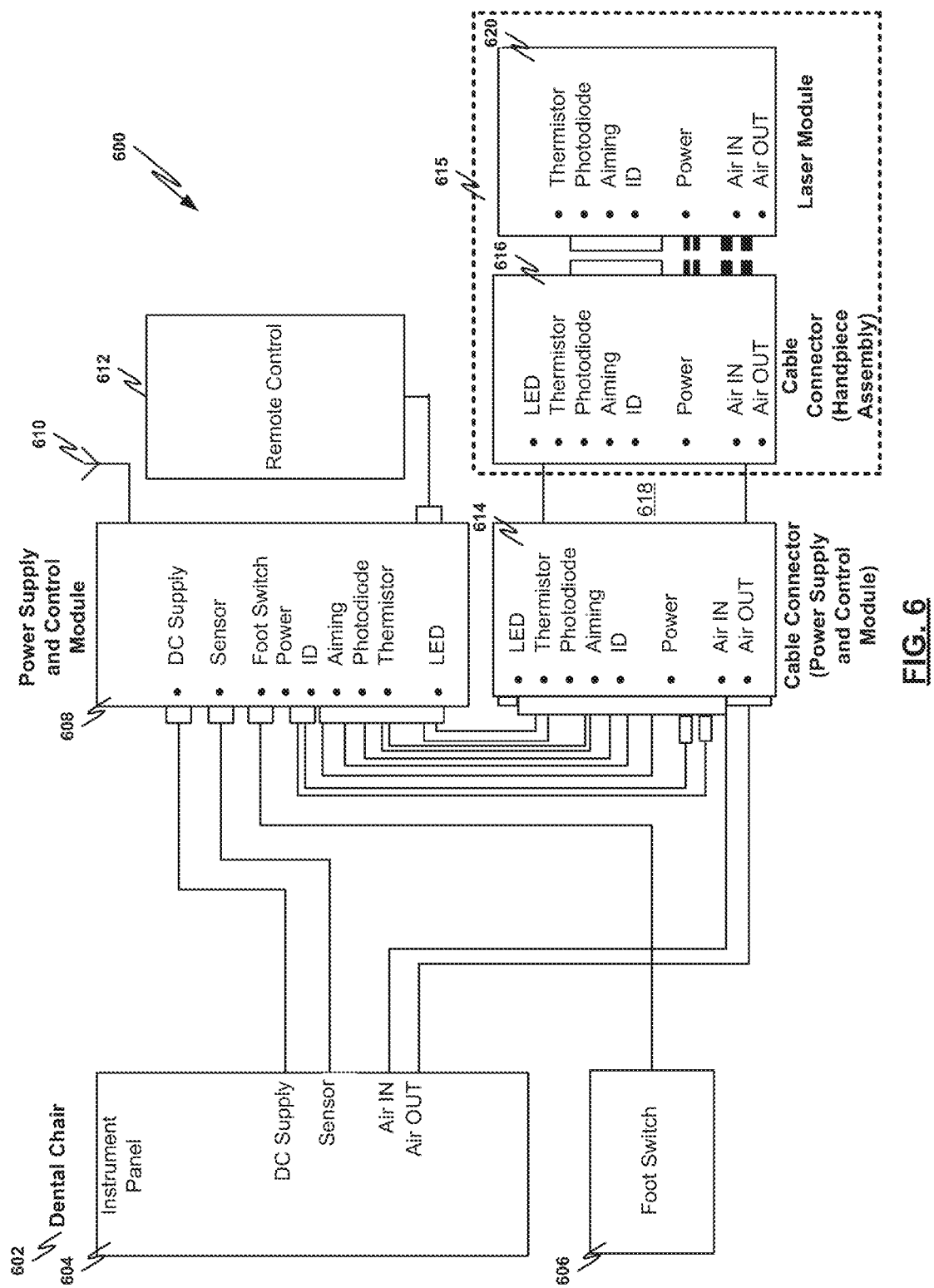
FIG. 6 depicts an example laser system illustrating exemplary connections between an instrument panel of a dental chair, a power supply and control module, and a handpiece assembly.

FIG. 6 depicts an example laser system 600 illustrating exemplary connections between an instrument panel 604 of a dental chair 602, a power supply and control module 608, and a handpiece assembly 615. In FIG. 6, cable connectors 614, 616, 620 of the power supply and control module 608, the handpiece assembly 615, and the laser module, respectively, are similar to those described above with reference to FIG. 5. The cable connector 616 of the handpiece assembly 615 is designed to match the cable connector 614 of the power supply and control module 608. With the matching connectors 614, 616, various signals and substances are transported between the power supply and control module 608 and the handpiece assembly 615. Specifically, the connectors 614, 616 include connections or channels for transferring a laser power control signal, air intake and output, an identification code signal, a signal from a thermistor, a signal from a photodiode, a signal from a light emitting diode, and an aiming beam. These signals and substances are transferred over the cable 618. The cable connector 616 of the handpiece assembly 615 also matches the connector 620 of the laser module. As illustrated in FIG. 6, the instrument panel 604 of the dental chair 602 is used to provide the air intake and output to the cable connector 614.

The power supply and control module 608 includes connections for connecting to the cable connector 614 and is thus configured to transmit the laser power control signal, the signal from the light emitting diode, and the aiming beam and to receive the identification code signal, the signal from the thermistor, and the signal from the photodiode. The power supply and control module 608 is also connected to the instrument panel 604, a footswitch 606, and a remote control 612. The instrument panel 604 of the dental chair 602 provides a DC supply voltage and a sensor output to the power supply and control module 608. The DC supply voltage is used by the power supply and control module 608 to provide a driving current to the laser module included in the handpiece assembly 615. The sensor output indicates whether the handpiece assembly 615 is within a holder included on the dental chair 602, and the sensor output is used in one example to automatically switch the laser system 600 between "standby" and "ready" modes.

The footswitch 606 provides a signal to the power supply and control module 608, where the signal is used to actuate the laser output of the handpiece assembly 615 when the laser system 600 is in the "ready" mode. The remote control 612 also provides a signal to the power supply and control module 608. Although the remote control 612 is depicted as being connected to the power supply and control module 608 via a wired connection, the remote control 612 may also be connected to the power supply and control module 608 via a wireless connection. For example, the power supply and control module 608 includes an antenna 610 for facilitating wireless communications with the remote control 612. The remote control 612 is used to actuate the laser output of the handpiece assembly 615, cause various control signals to be sent from the power supply and control module 608 to the handpiece assembly 615, or otherwise control one or more operations of the handpiece assembly 615.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents. For example, although the present disclosure is described in terms of a dental or medical device, it will be apparent to one skilled in the art that the systems described herein have applications outside of dental and medical applications.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Further, as used in the description herein and throughout the claims that follow, the meaning of "each" does not require "each and every" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive of" may be used to indicate situations where only the disjunctive meaning may apply.

It is claimed:

1. An assembly for laser treating a target surface, the assembly comprising a handpiece assembly including:
   a cable connector that is detachably coupled to a power supply and control module, the cable connector being configured to receive power and control signals from the power supply and control module;
   a handpiece configured and arranged to receive electromagnetic energy from a laser source and to direct the electromagnetic energy to the target surface;
   a laser module configured and arranged to receive the power and control signals from the cable connector and to generate electromagnetic energy based on the received power and control signals,
   the laser module being a particular laser module that is at least partially inserted into the handpiece and a cable connector at least partially inserted into the laser module, wherein the handpiece and the cable connector are detachably coupled to the particular laser module to allow the particular laser module to be removed from the handpiece assembly, and replaced with another laser module; and
   wherein the particular laser module is configured and arranged to be replaced with the another laser module without requiring replacement of the cable connector, the handpiece, or the power supply and control module; and
   wherein the handpiece is configured to-direct the electromagnetic energy from the laser module to the target surface.

2. The assembly of claim 1, wherein the particular laser module includes a light source of a first type, the first type being a laser diode, a diode-pumped solid state laser, a flashlamp-pumped solid state laser, or a light emitting diode; and
   wherein the another laser module includes a light source of a second type, the second type being different than the first type, and the second type being a laser diode, a diode-pumped solid state laser, a flashlamp-pumped solid state laser, or a light emitting diode.

3. The assembly of claim 1, wherein the particular laser module is configured to generate the electromagnetic energy of a first wavelength, and wherein the another laser module is configured to generate the electromagnetic energy of a second wavelength that is different from the first wavelength.

4. The assembly of claim 1, wherein the handpiece is replaceable, the replaceable handpiece allowing a particular handpiece to be removed from the handpiece assembly and replaced with another handpiece without requiring replacement of the cable connector, the laser module, or the power supply and control module.

5. The assembly of claim 4, wherein the particular handpiece is adapted for a first clinical operation, and wherein the another handpiece is adapted for a second clinical operation that is different from the first clinical operation.

6. The assembly of claim 5, wherein the first clinical operation is a surgery operation, a teeth-whitening operation, or a pain-therapy operation, and wherein the second clinical operation is a surgery operation, a teeth-whitening operation, or a pain-therapy operation.

7. The assembly of claim 1, wherein the handpiece assembly is detachably coupled to the power supply and control module via the cable connector and a cable, the detachable coupling allowing the handpiece assembly to be disconnected from the power supply and control module; and
   wherein the handpiece assembly is replaceable, the replaceable handpiece assembly allowing a particular handpiece assembly to be disconnected from the power supply and control module and replaced with another handpiece assembly without requiring replacement of the power supply and control module.

8. The assembly of claim 1, wherein the handpiece assembly does not include a fiber cable, and wherein a connection between the handpiece assembly and the power supply and control module does not include a fiber cable.

9. The assembly of claim 1, wherein the handpiece assembly is separate and distinct from the power supply and control, such that the power supply and control is not integrated within the handpiece assembly.

* * * * *